United States Patent
Schärer et al.

(10) Patent No.: US 8,371,746 B2
(45) Date of Patent: Feb. 12, 2013

(54) THERMAL ANALYSIS DEVICE

(75) Inventors: Corinne Schärer, Hinwil (CH); Ulrich Esser, Rüti (CH); Thomas Hütter, Niederrohrdorf (CH)

(73) Assignee: Mettler-Toledo AG, Greifensee (CH)

( * ) Notice: Subject to any disclaimer, the term of this patent is extended or adjusted under 35 U.S.C. 154(b) by 346 days.

(21) Appl. No.: 12/946,206

(22) Filed: Nov. 15, 2010

(65) Prior Publication Data

US 2011/0122913 A1 May 26, 2011

(30) Foreign Application Priority Data

Nov. 23, 2009 (EP) .................................... 09176757

(51) Int. Cl.
*G01K 17/00* (2006.01)
*G01N 25/20* (2006.01)

(52) U.S. Cl. .............. 374/10; 374/11; 374/31; 374/208; 422/51; 436/147

(58) Field of Classification Search ............. 374/10–12, 374/29, 30–39, 141, 208, 100; 436/147; 422/51

See application file for complete search history.

(56) References Cited

U.S. PATENT DOCUMENTS

| | | | | |
|---|---|---|---|---|
| 3,285,053 A * | 11/1966 | Mazieres | ......................... | 374/13 |
| 3,336,790 A * | 8/1967 | Nedumov | ....................... | 374/11 |
| 4,904,090 A * | 2/1990 | Oliver | .......................... | 374/124 |
| 6,523,998 B1 * | 2/2003 | Danley et al. | ................... | 374/12 |
| 6,535,824 B1 | 3/2003 | Mansky et al. | | |
| 6,626,567 B2 * | 9/2003 | Boiarski | ......................... | 374/11 |
| 7,104,681 B2 * | 9/2006 | Naranjo Carvajal | .......... | 374/143 |
| 7,753,582 B2 * | 7/2010 | Lopez et al. | .................... | 374/44 |
| 8,235,589 B1 * | 8/2012 | Feller | .............................. | 374/39 |
| 2003/0086473 A1 * | 5/2003 | Popelar et al. | ................ | 374/139 |
| 2008/0061808 A1 * | 3/2008 | Mok et al. | ..................... | 324/758 |
| 2012/0120986 A1 * | 5/2012 | Konno et al. | ................. | 374/179 |
| 2012/0315691 A1 * | 12/2012 | Carlsson et al. | ........... | 435/287.1 |

OTHER PUBLICATIONS

Benoist, L. et al., Integrated Circuit Thermal Analysis, A new thermal technique for polymer characterization, Journal of Thermal Analysis and Calorimetry, 2000, pp. 351-358, 59.

Doettinger-Zech, S.G. et al., Simple microcalorimeter for measuring microgram samples at low temperatures, Review of Scientific Instruments, May 2001, pp. 2398-2406, 72(5).

Van Herwaarden, A.W., Overview of calorimeter chips for various applications, Thermochimica Acta, 2005, pp. 192-201, 432.

Wang, L. et al., Demonstration of MEMS-based differential scanning calorimetry for determining thermodynamic properties of biomolecules, Sensors and Actuators B, 2008, pp. 953-958, 134.

* cited by examiner

*Primary Examiner* — Gail Verbitsky
(74) *Attorney, Agent, or Firm* — Standley Law Group LLP

(57) ABSTRACT

A thermal analysis device comprising a replaceable sensor that can be contacted via a contact element of an electrical contacting means, a heating element and a cooling element. The contact element(s) is thermally connected with the heating element and can be heated essentially independently of the operating state of the cooling element even when no sensor is mounted to the device.

24 Claims, 3 Drawing Sheets

THERMAL ANALYSIS DEVICE

CROSS-REFERENCE TO RELATED APPLICATIONS

This application is entitled to, and claims, benefit of a right of priority under 35 USC §119 from European patent application 09176757.4, filed on 23 Nov. 2009, the content of which is incorporated by reference as if fully recited herein.

TECHNICAL FIELD

The invention relates to a thermal analysis device with a replaceable sensor, such as a MEMS sensor.

BACKGROUND

The term thermal analysis may encompass various measurement methods, including inter alia, calorimetry, DSC (differential scanning calorimetry), TGA (thermo-gravimetric analysis), determination of a dielectric constant and also combinations of these methods.

The implementation of these methods on, with or by means of a suitable sensor, in particular a MEMS-based sensor (MEMS: Micro-Electro-Mechanical Systems), is particularly advantageous for the analysis of small samples or extreme thermal processes. Small samples are here understood as samples with dimensions in the sub-millimeter range and weights in the microgram and nanogram range.

A sensor in accordance with the invention is preferably a MEMS sensor, which includes an integrated circuit and which is configured in such a manner that a thermal analytical measurement can be carried out on a sample with or on this sensor. Preferably, this is a DSC or TGA-MEMS sensor, a MEMS sensor for the determination of the dielectric constant or a combination thereof, by use of which at least one thermal analytical property of a sample arranged on the sensor or associated with the sensor can be determined. It is possible to differentiate between active and passive sensors, an active sensor having active components, such as for example heating resistors, and a passive sensor for example being subjected to a temperature program by means of an external temperature control unit. Such sensors comprise at least one measuring position for a sample, but can also comprise a plurality of measuring positions for at least one sample and at least one reference. Hitherto, MEMS sensors have been primarily used in research laboratories. This use has made it possible to indicate the suitability of such MEMS sensors for thermal analytical processes and methods and has enabled improvements in sensor design.

A MEMS-based sensor, here also designated as a MEMS sensor, is suitable for the analysis of temperature-dependent phenomena of very small samples on account of its dimensions and thermal properties, and also enables very rapid heating and/or cooling rates compared to currently commercially available devices, as the components to be temperature controlled and also the sample have small thermal masses. A. W. van Herwaarden for example gives an overview of the use of different MEMS sensors as calorimeters for the analysis of very thin films and samples with masses in the microgram or even nanogram range in "Overview of calorimeter Chips for Various Applications", Thermochimica Acta, 432 (2005), 192-201.

Research devices with MEMS sensors are typically not suitable for commercial use, where the user generally expects high reproducibility as well as reliability of the measurement results, a short time expenditure per measurement, and also user-friendly handling. Further, open systems are typically used in a research laboratory, which allows the experimenter to intervene into the experiment set-up at any time in order to optimize the same or to adapt the same to a planned experiment.

In research, it has proven beneficial if the sample for investigation or measurement is applied directly onto the sensor. The investigation of temperature phenomena of the sample can also lead to the sample fusing with the sensor. Therefore, changing a sample can be associated with an exchange of the sensor.

For commercial devices direct intervention into the experiment set-up by means of the user is generally excluded or at least severely restricted in order to increase the user friendliness of a device. A simple and fast sample change is also required, which is neither desired nor necessary for research devices.

In particular, when the sensors are operated in the low temperature range, various problems can arise, such as for example condensation water formation or icing up of individual components or the entire device as a consequence of repeated heating/cooling cycles. Especially in relation to a commercial device, it is desirable to prevent condensation water formation, the penetration of condensation water into the device (above all into the electronics), and in particular icing up, in order to eliminate the arising of artifacts to the greatest extent possible. In addition, it is desirable if the downtimes or defrost times between two measurements is as short as possible and thus the sample throughput can be kept high.

The provision of a commercially usable thermal analysis device that can provide a stable and reproducible measurement behavior is, therefore, desirable. Preferably, such a device has a compact construction, allows for simple handling, in particular when exchanging or replacing the sensor, and requires only a short time expenditure per measurement.

SUMMARY OF THE GENERAL INVENTIVE CONCEPT

A thermal analysis device with a replaceable sensor, particularly a MEMS sensor, is such a device. Preferably, this device also comprises a sensor holder having a receptacle for the replaceable sensor, an electrical contacting means for contacting the sensor, a cooling element for cooling the thermal analysis device, and a heating element. The electrical contacting means comprises at least one contact element, which is in contact with the mounted sensor. The contact element is thermally connected with the heating element and can thus also be heated essentially independently of the operating state of the cooling element even when the sensor is dismounted.

In this manner, the sensor can, prior to replacement, be heated independently of the rest of the thermal analysis device to a desired or suitable temperature. The contact element can be heated independently of the operating state of the cooling element, in particular when the cooling element is running or active, and independently of the temperature of the rest of the thermal analysis device.

The sensor is designated as "mounted" or "installed" when it is located in the thermal analysis device, and as "dismounted" when it is not located therein.

A thermal analysis device of the present invention may be configured for passive or for active sensors, wherein active sensors are preferred. An active sensor includes integrated means for setting a predefined temperature program of temperature/time setpoint values. A passive sensor is thermally connected with an external temperature control unit, which is not integrated into the sensor, and with which temperature control unit the temperature of the sensor can be controlled. In case of a sensor exchange, an active sensor can be replaced completely. If a passive sensor is used, only the sensor and not the temperature unit are replaced. The external temperature control unit is preferably a part of the thermal analysis device. In addition, the thermal analysis device may be used for controlling a sensor arranged in the device, by means of which the thermal analytical properties of a sample connected with the sensor can be determined. Additionally, the thermal analysis device may be used to determine thermal or thermal analytical properties of the MEMS sensor itself, in order to obtain e.g., information relating to its thermal stability or its functionality at different temperatures. The sensor may comprise at least one measuring position for a sample, or a plurality of measuring positions for at least one sample and at least one reference.

It is advantageous for such a thermal analysis device that particularly the temperature of the components in the vicinity of the receptacle for the sensor, and also the temperature of a mounted sensor, can be controlled and regulated, so that a sensor can be exchanged or replaced rapidly and simply even while maintaining very low temperatures in the interior of the thermal analysis device. The simple and rapid replacement of the sensor is made possible in that the temperature of the contact element can be changed or set independently of the operating state of the cooling element. Therefore, the contact element can be heated when the cooling element is running and also independently of the temperature of the remainder of the thermal analysis device. In addition to a simple and rapid replacement of the sensor, the reproducibility of the measurement results is also improved in this manner, as, following an exchange of the sensor, it is possible to cool down the sensor again in a very rapid manner and with a high cooling rate so that thermal analytical measurements can be carried out entirely or to some extent at cryogenic temperatures or cryogenic initial temperatures. "Cryogenic temperatures" are herein understood to be temperatures that lie clearly below 0° C., preferably in a range of approx. −20° C. to the region of the thermodynamic zero point, in particular down to approximately −200° C.

The heating element and/or the cooling element can be used for controlling the temperature of the thermal analysis device, more precisely, the components thermally connected with the same and the interior of the thermal analysis device, so that these components and the interior of the thermal analysis device can be adjusted to a predetermined temperature or subjected to a temperature program that includes predetermined temperature/time values.

The replacement of the sensor can be carried out without the cooling element having to be switched off and/or the entire thermal analysis device having to be heated, as the contact element can be heated independently of the operating state of the cooling element even when the cooling element is active or running. As a result a rapid replacement of the sensor as well as, following mounting of the same, rapid cooling to a desired initial temperature is enabled.

The selected heating of certain components of the thermal analysis device, in particular of the contact element, is additionally advantageous, as an icing up of the thermal analysis device during operation can substantially be prevented. This improves and positively influences the reproducibility of the results as well as lengthens the life of the contact elements and also of further electrical and electronic components of the device.

One end of the contact element is connected with the socket of the contacting means. The other end is a free end for contacting the sensor. In a preferred configuration, the contact element comprises a stop adjacent to its free end. The contact element is thermally connected with the heating element when the sensor is mounted and also when it is dismounted, so that, during removal or exchange, the temperature of the contact element can be regulated independently of the remainder of the thermal analysis device and the sensor.

The thermal contact between the heating element and the contact element is established via a stop at the free end of the contact element in the case of a dismounted sensor and, with the sensor mounted, via the contact of the free end with the sensor.

If the sensor is located in the thermal analysis device, then the latter is electrically contacted via the free end of the contact element. The contact element is in thermal and electrical contact with the sensor and can be heated via the sensor and the sensor holder, which is preferably thermally connected with the heating element.

If there is no sensor mounted in the thermal analysis device, then the contact element is thermally connected with the heating element via its stop.

The thermal mass of the entire device is preferably large compared with the thermal masses of the components thermally connected with the heating element, so that a rapid heating of individual components or a plurality of these components is possible even when the cooling element is running.

Furthermore, the device can include a spacer that is thermally conductive and electrically insulating, has a leadthrough for the contact element, and is thermally connected with the heating element. This spacer is preferably connected with the sensor holder on the side of the sensor holder opposite the receptacle and is used as counter-stop for the stop of the contact element, so as to push against the spacer when the sensor is dismounted, thus establishing thermal contact with the heating element.

The electric contacting means comprises one or a plurality of contact elements for direct contacting of the replaceable sensor. The contact elements and the sensor are configured in such a manner that a releasable electrical connection can be established. The contact elements can, for example, be spring contacts onto which the sensor is pushed, or the sensor can comprise pins that engage or snap into pre-tensioned contact elements, for example resilient elements such as clips or clasps.

The contact elements essentially consist of a thermally and electrically conductive material, for example a metal or a metal alloy, in particular gold, silver, platinum or mixtures thereof.

The contact element is preferably used in a pre-tensioned manner so that the stop pushes against the spacer when the sensor is dismounted, and is thermally connected via the spacer and the sensor holder with the heating element. For installation, the sensor is pushed by means of a fixing element onto the contact elements, so that electrical contact with the sensor is established. In addition, thermal contact between the stop and the spacer is interrupted when the sensor is mounted. The interruption of contact with the spacer is important, as the system would otherwise be mechanically over-defined, such that the thermal contact could cause failures during a measurement. The mounted sensor further closes off the region of the thermal analysis device containing the contact element, as a result of which a flooding of the interior of the thermal analysis device with a purge or dry gas is enabled. This additionally reduces condensation water formation and ice formation.

The contacting means may comprise a plurality of contact elements, so that various circuit elements on the mounted sensor can be contacted directly in order to transfer electrical signals between at least one external or internal control unit and the sensor.

In this manner, the temperature of the at least one contact element may be increased independently of the temperature of the device and independently of the operating state of the cooling element by means of the heating element. This temperature increase can be carried out both with the sensor mounted and dismounted.

In a preferred configuration, an insulator is arranged between the cooling element and the heating element. The insulator may, for example, be constructed as a flat disc made of a plastic such as PMMA. In any case, the insulator material should be an electrical and/or thermal insulator and, additionally, should not absorb water or should only be able to absorb as little water as possible. Stored or embedded water would change the insulation properties and could, through freezing, even cause damage to the insulator. The insulator material and also its strength are chosen so that the thermal resistance of the insulator is adapted to the heating power of the heating element. In this way, the heating element can heat against the insulator, which limits the heat propagation within the thermal analysis device, at least to some extent. By choosing a suitable insulating material adapted to the heating power of the heating element, the quantity of energy required for heating or keeping the temperature of the sensor constant can be optimized and preferably kept small. In addition, a rapid heating of the sensor is enabled without the cooling element having to be switched off or heated. Preferably, an exchange of the sensor takes place at temperatures above zero degrees centigrade, preferably at temperatures between approximately 10° C. and approximately 50° C., in particular up to approximately 35° C., whereby it should be possible for the sensor preferably to be cooled to the desired initial temperature again within less than 30 minutes.

The heating element is preferably a flat heater or a wire, which may be arranged in a spiral or meandering manner on the insulator, a side of the sensor holder or a separate carrier element. The heating element is arranged between the sensor holder and the insulator.

In a further embodiment, the heating element may comprise a warm air source, the air or gas flow of which is directed onto the sensor holder.

The cooling element can be connected with an external cooler, so that the device can be cooled to cryogenic temperatures. The external cooler may be, for example, a cryostat, an intracooler or a cryogenic-fluid line, using a liquid gas such as nitrogen or helium.

The combination of the sensor holder, heating element, insulator, and cooling element with connected cooler, enables the rapid exchange of the sensor, already described previously, independently of the operating state of the cooling element, even at low and very low temperatures in the interior of the thermal analysis device. In addition, this combination also prevents ice formation within the device, which is practically unavoidable with known research equipment and devices during an exchange of the sensor.

Thermal analytical measurements should be carried out under conditions that are as reproducible as possible. So, it is advantageous if a uniform and above all, reproducible, atmosphere prevails in the thermal analysis device. In order to achieve this, the insulator, the sensor holder and the replaceable sensor include passages, which are used for letting through and for directing a gas flow. Inert gases such as for example nitrogen or argon may be used as gases. Furthermore, the use of reactive gases that can react with the sample in order, for example, to investigate oxidation processes, would also be possible. The passages are arranged so that the gas flow does not significantly influence the measurement. The flooding of the thermal analysis device with a suitable gas additionally has the advantage that the condensation of water and also ice formation can be prevented or at least strongly reduced.

In addition to the at least one contact element, the contacting means includes a socket, to which an end of the contact element is connected. In addition, the contacting means is electrically connected with a control unit via a connection means with a high thermal resistance.

The at least one control unit is preferably configured so that, on the one hand, it controls and regulates the device and, on the other hand, detects and evaluates measurement data for the determination of analytical properties of a sample on the sensor or of the sensor itself. Of course, it is also possible that the data detected by the control unit is forwarded to a further external unit for evaluation.

The contact elements are connected with the control unit via a connection means or an electrical line, which can be, for example, a cable with a multiplicity of wires insulated with respect to one another and with respect to the outside. The connection means may include, for example, a plug or a solder connection for connecting the electrical line with the contact elements or the contacting means.

Furthermore, the sensor holder may comprise a positioning aid for the replaceable sensor, which delimits the receptacle. Preferably, the positioning means comprises a plurality of positioning elements that are arranged and/or configured in such a manner that the sensor can only be mounted in a predetermined orientation into the receptacle.

The sensor can be fixed on the sensor holder by means of a fixing element. In addition, the fixing element is used to push the mounted or installed sensor into the receptacle, so that an electrical contact with the contacting means can be established.

The fixing element can have a recess, which leaves a part of the surface of the replaceable sensor open. This recess allows the user to apply a sample onto the sensor mounted and fixed into the device and/or to optically monitor its behavior during a measurement.

The previously described thermal analysis device may essentially be arranged in a thermally insulated housing, which preferably includes one or a plurality of thermal insulations. Furthermore, the housing may comprise an optically transparent lid, so that the user can optically monitor the processes in the interior of the device.

The at least one control unit connected with the thermal analysis device is used for the regulation of the various temperatures within the thermal analysis device as well as for controlling the measurement on or by means of the sensor. The control unit may be configured as an internal or as an external unit.

The thermal analysis device may further include at least one temperature probe, which is connected with the control unit so that the measured values can be used for setting the temperature control device. With the at least one temperature probe, the actual temperature, the temperature of the sensor holder, and/or the temperature at any desired other position within the thermal analysis device can be determined.

A suitable replaceable sensor for a thermal analysis device of this type may include at least one measuring position for a sample, a sensor temperature controlling device, a means for setting a predetermined temperature program of temperature/time setpoint values and at least one means assigned to the measuring position for signal detection, in particular, for temperature detection, so that at least one thermal analytical property of a sample arranged on the sensor can be determined with the device. The sensor is preferably a MEMS sensor.

Preferably, the means for setting a predetermined temperature program of temperature/time setpoint values is integrated in the sensor, for example, in the form of an electrical resistance heater that is constructed as part of the sensor circuit and is thermally connected with the measuring position. A sensor configured in this manner is herein designated as an active sensor.

In a further embodiment, the sensor is configured as a heat flux sensor. For this purpose, the means for temperature detection may be constructed and arranged in the form of thermocouples likewise directly on the sensor. The sensor itself, interacting with the control unit, may thus provide the functions of a thermal analysis device and is used for investigating and measuring the temperature-dependent properties of a sample, which is subjected to a temperature program. Therefore, the sensor is mounted into the thermal analysis device connected with the control unit.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Figure 1:
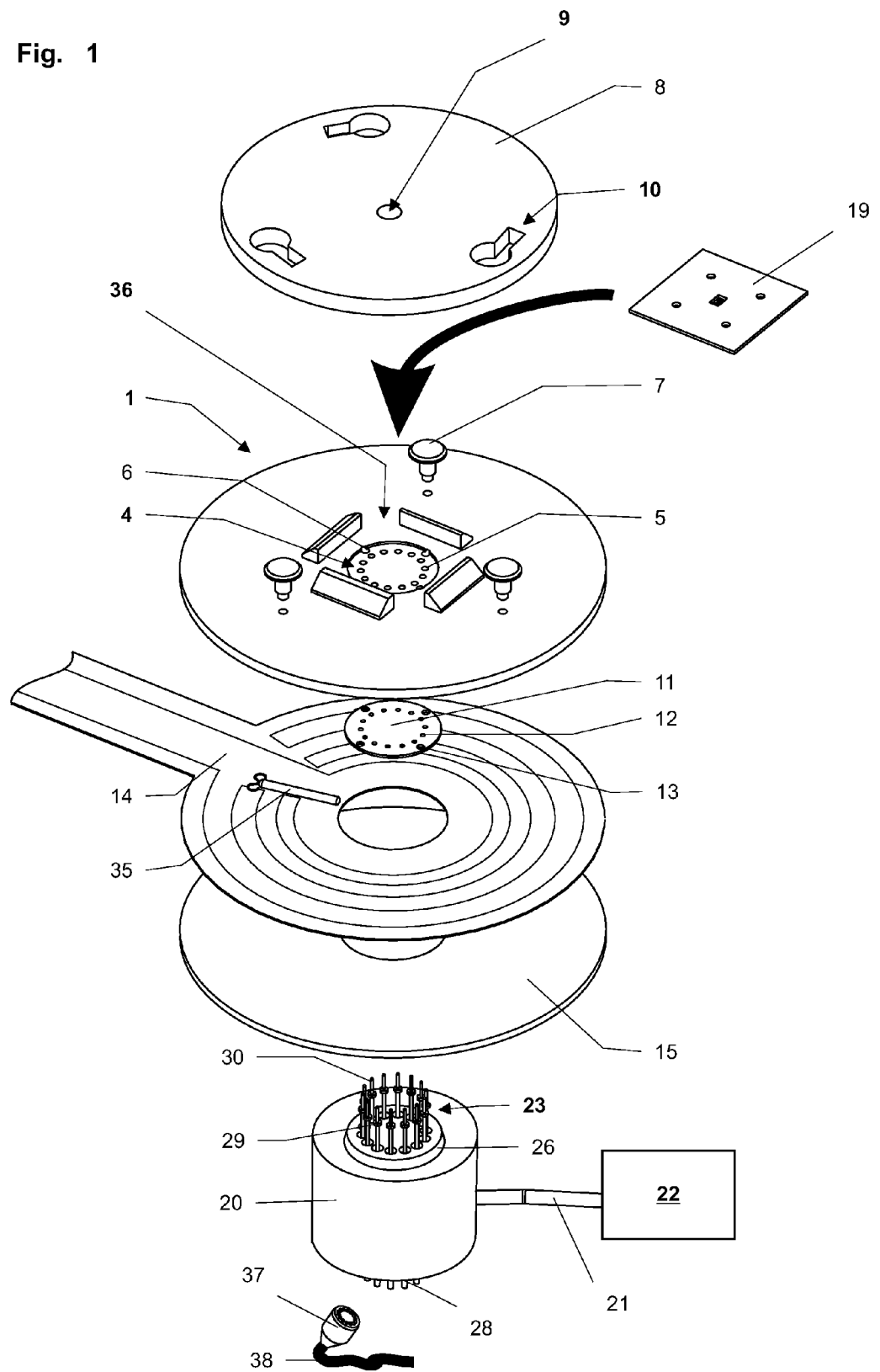
FIG. 1 shows an exploded view of an exemplary thermal analysis device of the present invention.

FIG. 1 shows an exploded view of an exemplary thermal analysis device (also referred to hereafter as "device") according to the present invention. Connection and/or fixing means, as well as associated leadthroughs between the components are, with a few exceptions, not shown in the figures for reasons of clarity.

A fixing element 8 is arranged so that it can push a sensor 19 located in a receptacle 36 against a contacting means, and fix it on a sensor holder 1. The fixing element 8 includes a central recess 9, which in the assembled state exposes a part of the sensor 19, in particular a measuring position arranged on the sensor 19, so that the sensor 19 can, for example, be fed with a sample or so that changes of the sample or of the sensor 19 can be optically monitored. Preferably, the sensor 19 is a DSC, TGA-MEMS sensor, a MEMS sensor for the determination of the dielectric constant, or a combination thereof, by use of which at least one thermal analytical property of a sample arranged on the sensor 19 or associated with the sensor 19 can be established.

For fixing on the pins 7 of the sensor holder 1, the fixing element 8 comprises a plurality of snap-in aids 10, into each of which a head of the pin 7 can be engaged. Depending on the configuration of the sensor holder 1 and of the fixing element 8, other releasable fixing systems with suitable fixing elements, well-known to the person skilled in the art, can also be used.

The device further includes a thermally conductive and electrically insulating spacer 11, which is fastened on the side of the sensor holder 1 that faces away from the receptacle 36. The spacer 11 is preferably a ceramic disc made from aluminium nitride with a second leadthrough 12 for each contact element in each case. Instead of aluminium nitride, other ceramic materials with similar properties can also be used. The positions of the second leadthroughs 12 match those of the first leadthroughs 5 in the sensor holder 1, so that the contacting means is guided contactlessly in the first and/or second leadthroughs 5, 12. In addition, the spacer can, as shown here, comprise one or a plurality of second gas passages 13. The spacer 11 is in particular used for establishing thermal contact between a heating element 14 and the contact elements for the dismounted sensor 19, i.e., when there is no sensor 19 in the receptacle 36.

The heating element 14 is here configured as a flat heater with a central recess. The heating element 14 is arranged between the sensor holder 1 and an insulator 15, so that the heating element 14 can heat at least the sensor holder 1, the spacer 11, the contact elements 23 and also the mounted sensor 19. The contact elements 23 are thermally contacted via the sensor holder 1 and the mounted sensor 19 or, when the sensor 19 is dismounted, via the spacer 11. Additionally, the heating element 14 comprises a temperature probe 35 for measuring and regulating its temperature.

Furthermore, the thermal analysis device can, as shown here, comprise a gas inlet through which a gas may be introduced into the thermal analysis device and allowed to flow through the gas passages 6, 13 in the sensor holder 1 and spacer 11. A dry inert gas, such as nitrogen, argon or helium is preferably used, so that an inert gas atmosphere can propagate around the sample or the sensor, as a result of which the influences of the environment on a measurement can be minimized. Alternatively, a reactive gas can be used, so that for example oxidation processes or other reactions and processes can be investigated.

The insulator 15 is here constructed in a disc-shaped manner and consists of a material such as for example PMMA. The material and also its strength are preferably chosen so that the thermal resistance of the insulator 15 is adapted to the heating output of the heating element 14. This way the heating element 14 heats against the insulator 15, which strongly reduces the heat propagation through the insulator 15 in the direction of the cooling element 20. By choosing a suitable insulating material adapted to the heating power of the heating element 14 and with a suitable thickness, the amount of energy required for heating or keeping the temperature within the thermal analysis device (and in particular the temperature of the sensor 19) constant can be optimized and preferably kept small.

Furthermore, the thermal analysis device includes a contacting means with a socket 26, in which a plurality of contact elements 23 are arranged. The contacting means also has a connector 28, which can be attached via a suitable plug 37 to an electrical line 38, for example a cable, or connected with the same. The plug 37 and the cable 38 are shown herein only for purposes of illustration, and are not shown true to scale. The cable 38 can also be securely connected to the connector 28 via a solder connection. In order to prevent unnecessary heat transfer into the device by means of the electrical line, this should have a thermal resistance that is as high as possible and which can be influenced by means of the length of the electrical line.

Each of the contact elements 23 have a free end 30 directed towards the sensor 1 or the spacer 11 and an opposite end fixed in a socket 26. Preferably, the contact elements 23 have spring contacts and each comprises a stop 29 at some distance from its free end 30. The spring contacts 23, as well as the stops 29, consist of an electrically and thermally conductive material, such as for example gold, silver, platinum or mixtures thereof. The free ends 30 project through the second leadthroughs 12 in the spacer 11 and the first leadthroughs 5 in the sensor holder 1 of an operational thermal analysis device. On account of the stops 29, the spring contacts 23 are pushed against the spacer 11 when the sensor 19 is dismounted. In this state, the spring contacts 23 can be heated by the heating element 14 via contact between the stop 29, the spacer 11 and the sensor holder 1. As a result, condensation water formation or icing up can be prevented to the greatest possible extent during exchange of the sensor 19 (see FIGS. 4 and 5).

This contacting of the contacting means is in particular advantageous if the interior of the thermal analysis device should be cooled to cryogenic temperatures by means of a cooling element 20, as a rapid defrosting of the installed sensor 19 and the contact elements 23 is possible without switching off the cooling element 20 and also without defrosting of the entire thermal analysis device. As a result, following the mounting of another sensor, said sensor can then be rapidly cooled. The cooling element 20 is essentially annularly designed, at least partially surrounds the electrical contacting means, and comprises at least one connector 21 for connecting an external cooler 22. The external cooler may be, for example an intracooler, a cryostat or a cryogenic-fluid line that uses, for example, liquid nitrogen or liquid helium.

Figure 2:
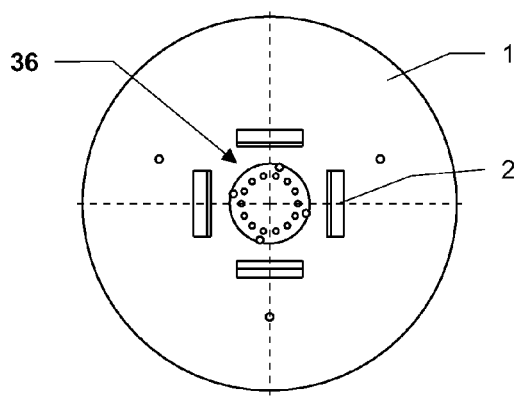
FIG. 2 shows a top view of an exemplary sensor holder with positioning aids.

FIG. 2 shows a top view of the sensor holder 1 of FIG. 1. In the top view, four positioning aids 2 are shown, which delimit the receptacle 36 for the sensor.

Figure 3:
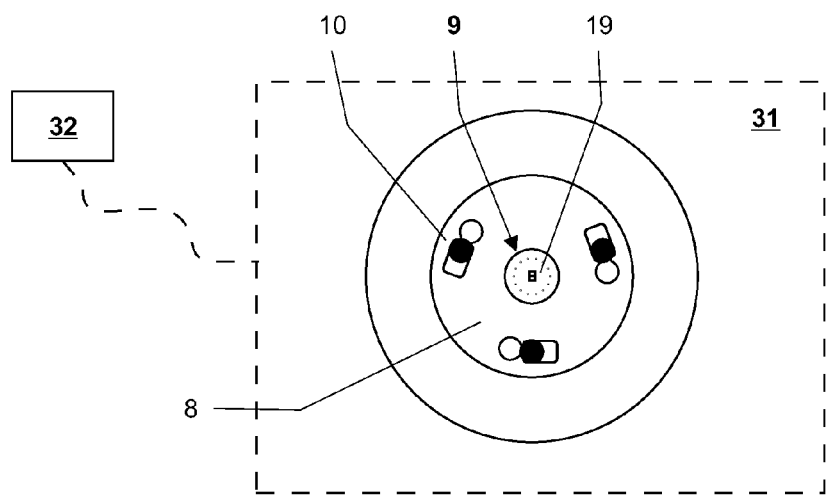
FIG. 3 shows a top view of an exemplary thermal analysis device arranged in a housing.

FIG. 3 shows a top view of a thermal analysis device in a thermally insulated housing 31. The housing 31 is only indicated schematically. In the top view, it can be seen that, in operation or in the assembled state, the recess 9 in the fixing element 8 leaves a part of an installed sensor 19 exposed, so that, for example, this can be loaded with a sample. The thermal analysis device is further connected to a control unit 32, as is indicated here, which control unit comprises means for controlling and regulating the thermal analysis device and the sensor 19 and also for data detection and/or evaluation of the measurement data.

Figure 4:
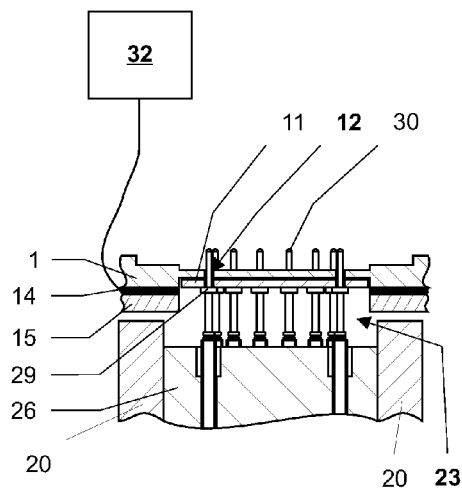
FIG. 4 shows a schematic and cross-sectional partial view of an exemplary thermal analysis device without a sensor.
Figure 5:
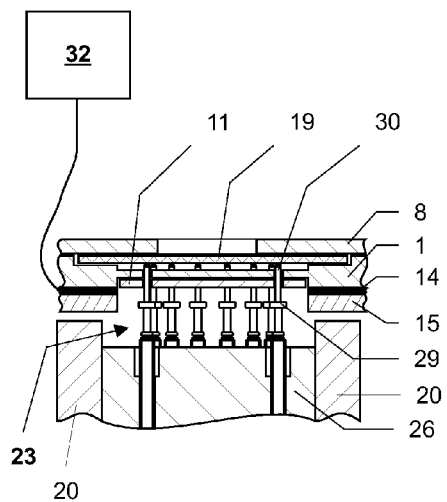
FIG. 5 shows a schematic and cross-sectional partial view of an exemplary thermal analysis device with a mounted sensor.

FIGS. 4 and 5 show a detailed view of the contacting of a mounted sensor 19 by means of the contacting means and also the thermal connection of the contacting means or, more precisely, the at least contact element 23 with the heating element 14. Both figures show a schematic partial view of the device, wherein the components thereof may not be shown true to scale.

FIG. 4 shows a schematic partial view, in cross section, of the thermal analysis device without a sensor (or with dismounted sensor). In either case, one end of the contact elements 23 is guided and held in the socket 26 of the contacting means, which is surrounded by a cooling element 20. The free ends 30 of the contact elements 23 extend without contact through corresponding leadthroughs 12 in the spacer 11. Additionally, the spacer 11 serves, when the sensor is removed or dismounted, as a counter-stop for the stop 29 of each contact element 23, which stop 29 is arranged near the free end 30 of the contact element 23 and which contact element 23 is here configured as a spring contact or spring contact pin and is mounted in a pre-tensioned fashion.

The spacer 11 is arranged in a recess of the sensor holder 1 and 15 thermally connected with the same. The sensor holder 1 is in turn in contact with the heating element 14, which is controlled by means of the control unit 32, which is connected with the device. The heating element 14 is arranged between the sensor holder 1 and the insulator 15, the insulator 15 and the heating element 14 being matched to one another so that for an active cooling element as little heat as possible penetrates the insulator 15.

As long as no sensor is located in the thermal analysis device, the stops 29 of the contact element 23 push against the spacer 11 forming the counter-stop and can so be heated or maintained at a predetermined temperature by means of the heating element 14, independently of the operating state of the cooling element 20 and the temperature within the thermal analysis device.

FIG. 5 shows the same schematic partial view of the device as FIG. 4, but with the sensor 19 mounted to the sensor holder 1. The sensor 19 is pushed with the fixing element 8 onto the contact elements 23, which are pushed together as a result. This way, on the one hand, electrical contact with the contact elements 23 is established and, on the other hand, the stops 29 of the contact elements 23 are pushed by the spacer 11 toward or against the socket 26 so that the stops 29 no longer push against the spacer 11. Thermal contact between the contact elements 23 and the heating element 14 is then established by means of the sensor 19 and the sensor holder 1.

Figure 6:
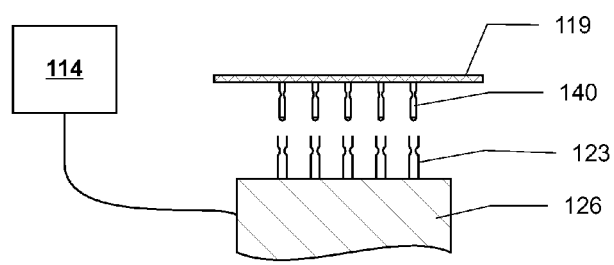
FIG. 6 shows a schematic view of further exemplary embodiments of a contacting means and sensor.

FIG. 6 shows a further embodiment of a contacting means and a sensor 119 for a thermal analysis device according to the invention. The sensor 119 comprises pins 140, which can snap into a contacting means 123 that are configured in the manner of a leaf spring. The contacting means can, as indicated here, also be thermally connected with a heating element 114 via a socket 126.

LIST OF REFERENCE SYMBOLS USED HEREIN

1 Sensor holder
2 Positioning aid
4 Sunken region
5 First leadthrough
6 First gas passage
7 Pin
8 Fixing element
9 Recess
10 Snap-in aid
11 Spacer
12 Second leadthrough
13 Second gas passage
14, 114 Heating element/flat heater
15 Insulator
19, 119 Sensor
20 Cooling element
21 Connector for cooler
22 Cooler
23, 123 Contact element
26, 126 Socket
28 Connector
29 Stop
30 Free end
31 Housing
32 Control unit
35 Temperature probe
36 Receptacle
37 Plug
38 Electrical line/cable
39 Contact pin
140 Pin Although the invention has been described by means of the specific exemplary embodiments, it is obvious that numerous further embodiments may be created given knowledge of the present invention, for example, in that the features of the individual exemplary embodiments are combined with one another and/or individual function units of the exemplary embodiments are exchanged. Therefore, while certain embodiments of the present invention are described in detail above, the scope of the invention is not to be considered limited by such disclosure, and modifications are possible without departing from the spirit of the invention as evidenced by the following claims:

What is claimed is:

1. A thermal analysis device with a replaceable sensor, comprising:
   a sensor holder having a receptacle for the replaceable sensor;
   an electrical contacting means for contacting the replaceable sensor, the electrical contacting means including at least one contact element that is in contact with the replaceable sensor when the sensor is mounted to the sensor holder;
   a cooling element for cooling the thermal analysis device; and
   a heating element, the heating element thermally connected with the at least one contact element such that the at least one contact element can be heated substantially independently of the operating state of the cooling element when the replaceable sensor is not mounted to the sensor holder.

2. The thermal analysis device of claim 1, wherein the replaceable sensor is a MEMS sensor.

3. The thermal analysis device of claim 1, wherein the at least one contact element includes a free end for contacting the replaceable sensor and a stop near the free end, such that the at least one contact element is thermally connected with the heating element via the free end thereof when the replaceable sensor is mounted to the sensor holder and via the stop when the replaceable sensor is not mounted to the sensor holder.

4. The thermal analysis device of claim 1, further comprising a spacer that is thermally conductive and includes a leadthrough for each contact element present.

5. The thermal analysis device of claim 4, wherein the spacer is electrically insulating.

6. The thermal analysis device of claim 1, further comprising an insulator arranged between the cooling element and the heating element.

7. The thermal analysis device of claim 6, wherein the insulator and the sensor holder include first and second passages for letting through and for steering a flow of gas.

8. The thermal analysis device of claim 1, wherein the heating element is a wire or flat heater.

9. The thermal analysis device of claim 1, wherein the cooling element is connected to an external cooler capable of cooling the device to cryogenic temperatures.

10. The thermal analysis device of claim 1, wherein the electrical contacting means is electrically connected with a control unit via a connection means with a high thermal resistance.

11. The thermal analysis device of claim 1, wherein the sensor holder includes a positioning aid for positioning the replaceable sensor.

12. The thermal analysis device of claim 1, further comprising a fixing element for affixing the replaceable sensor to the sensor holder.

13. The thermal analysis device of claim 1, wherein the replaceable sensor further includes:
   at least one measuring position for a sample;
   a temperature control device;
   a means for setting a predetermined temperature program of temperature/time setpoint values; and
   at least one means, assigned to the measuring position, for temperature determination, so that at least one thermal analytical property of a sample arranged on the replaceable sensor may be determined with the thermal analysis device.

14. The thermal analysis device of claim 13, wherein the means for setting a predetermined temperature program of temperature/time setpoint values is integral to the replaceable sensor.

15. The thermal analysis device of claim 13, wherein the replaceable sensor is configured as a heat flux sensor.

16. The thermal analysis device of claim 1, wherein the device is substantially arranged in a thermally insulated housing.

17. A thermal analysis device with a replaceable MEMS sensor, comprising:
   a sensor holder having a receptacle for the replaceable MEMS sensor;
   an electrical contacting means for contacting the replaceable MEMS sensor, the electrical contacting means including at least one contact element that is in contact with the replaceable MEMS sensor when the sensor is mounted to the sensor holder;
   a cooling element for cooling the thermal analysis device; and
   a heating element, the heating element thermally connected with the at least one contact element such that the at least one contact element can be heated substantially independently of the operating state of the cooling element when the replaceable MEMS sensor is not mounted to the sensor holder.

18. The thermal analysis device of claim 17, wherein the at least one contact element includes a free end for contacting the replaceable sensor and a stop near the free end, such that the at least one contact element is thermally connected with the heating element via the free end thereof when the replaceable MEMS sensor is mounted to the sensor holder and via the stop when the replaceable MEMS sensor is not mounted to the sensor holder.

19. The thermal analysis device of claim 17, further comprising a thermally conductive and electrically insulating spacer that includes a leadthrough for each contact element present.

20. The thermal analysis device of claim 1, further comprising an insulator arranged between the cooling element and the heating element, the insulator and the sensor holder both including first and second passages for letting through and for steering a flow of gas.

21. The thermal analysis device of claim 17, wherein the replaceable MEMS sensor further includes:
   at least one measuring position for a sample;
   a temperature control device;
   a means for setting a predetermined temperature program of temperature/time setpoint values; and
   at least one means, assigned to the measuring position, for temperature determination, so that at least one thermal analytical property of a sample arranged on the replaceable sensor may be determined with the thermal analysis device.

22. The thermal analysis device of claim 21, wherein the means for setting a predetermined temperature program of temperature/time setpoint values is integral to the replaceable MEMS sensor.

23. The thermal analysis device of claim 21, wherein the replaceable MEMS sensor is configured as a heat flux sensor.

24. The thermal analysis device of claim 17, wherein the device is substantially arranged in a thermally insulated housing.

* * * * *